US009907951B2

(12) United States Patent
Régnier et al.

(10) Patent No.: US 9,907,951 B2
(45) Date of Patent: Mar. 6, 2018

(54) SYSTEM IMPLANTABLE INTO THE CORONARY VENOUS NETWORK FOR THE STIMULATION OF A CARDIAC LEFT CAVITY

(71) Applicant: SORIN CRM SAS, Clamart (FR)

(72) Inventors: Willy Régnier, Longjumeau (FR); Nicolas Shan, Juvisy sur Orge (FR); Jean-François Ollivier, Villiers le Bacle (FR)

(73) Assignee: SORIN CRM SAS, Clamart (FR)

( * ) Notice: Subject to any disclaimer, the term of this patent is extended or adjusted under 35 U.S.C. 154(b) by 126 days.

(21) Appl. No.: 14/290,718

(22) Filed: May 29, 2014

(65) Prior Publication Data
US 2014/0358160 A1    Dec. 4, 2014

(30) Foreign Application Priority Data

Jun. 4, 2013  (FR) ...................................... 13 55126

(51) Int. Cl.
*A61N 1/05*        (2006.01)
*A61M 25/00*     (2006.01)
(Continued)

(52) U.S. Cl.
CPC ....... *A61N 1/0565* (2013.01); *A61M 25/0021* (2013.01); *A61N 1/056* (2013.01);
(Continued)

(58) Field of Classification Search
CPC ........ A61N 1/05; A61N 1/056–1/0597; A61N 1/37205; A61N 1/36182; A61N 1/36185; A61M 25/0021; A61M 2025/0042
See application file for complete search history.

(56) References Cited

U.S. PATENT DOCUMENTS 5,499,981 A * 3/1996 Kordis ................. A61B 5/0422
606/41
5,651,767 A * 7/1997 Schulman ................ A61N 1/05
600/372
(Continued)

FOREIGN PATENT DOCUMENTS

EP    0 993 840 A1    4/2000
EP    2 275 170 A1    1/2011
(Continued)

OTHER PUBLICATIONS

Preliminary Search Report for French Patent Application No. 1355126, dated Oct. 18, 2013, 2 pages.

*Primary Examiner* — Shaun L David
(74) *Attorney, Agent, or Firm* — Foley & Lardner LLP

(57) ABSTRACT

This system includes a conductor microcable and an insulating microcatheter, including a hollow tube housing the microcable with the possibility of relative axial translation therebetween. The microcatheter is suitable for permanent implantation. The microcatheter, in its distal portion, includes at least one lateral window formed by a through orifice formed on the wall of the hollow tube. The window forms a stimulation site defined on the wall of the target vein facing the window of the microcatheter, and provides for a region of the microcable surface located at the window to form a stimulation electrode. In its distal portion, the microcable is not isolated at least in the region of the window of the microcatheter. The microcatheter is telescopically moveable on the microcable, so as to modify the position of the stimulation site of the target vein.

20 Claims, 4 Drawing Sheets

(51) Int. Cl.
  *A61N 1/362* (2006.01)
  *A61N 1/372* (2006.01)
(52) U.S. Cl.
  CPC ............. *A61N 1/362* (2013.01); *A61N 1/372* (2013.01); *A61M 2025/0042* (2013.01)

(56) References Cited

U.S. PATENT DOCUMENTS

| | | | | |
|---|---|---|---|---|
| 5,824,030 | A * | 10/1998 | Yang | A61N 1/056 600/374 |
| 6,090,104 | A * | 7/2000 | Webster, Jr. | A61B 18/1492 600/374 |
| 9,031,647 | B2 * | 5/2015 | Maskara | A61B 5/0422 600/374 |
| 2002/0183817 | A1 * | 12/2002 | Van Venrooij | A61N 1/0534 607/116 |
| 2004/0024425 | A1 * | 2/2004 | Worley | A61N 1/056 607/27 |
| 2006/0247751 | A1 | 11/2006 | Seifert | |
| 2010/0331938 | A1 * | 12/2010 | Sommer | A61N 1/0534 607/116 |
| 2011/0046713 | A1 * | 2/2011 | Cully | A61F 2/07 623/1.13 |
| 2011/0190786 | A1 * | 8/2011 | Gerber | A61B 17/00 606/129 |
| 2011/0218602 | A1 * | 9/2011 | Kampa | A61N 1/05 607/116 |
| 2012/0130464 | A1 * | 5/2012 | Ollivier | A61N 1/056 607/122 |
| 2013/0166007 | A1 * | 6/2013 | True | A61N 1/36 607/116 |

FOREIGN PATENT DOCUMENTS

| | | |
|---|---|---|
| EP | 2 455 131 A1 | 5/2012 |
| EP | 2 559 453 A1 | 2/2013 |
| EP | 2 581 107 A1 | 4/2013 |

* cited by examiner

SYSTEM IMPLANTABLE INTO THE CORONARY VENOUS NETWORK FOR THE STIMULATION OF A CARDIAC LEFT CAVITY

CROSS-REFERENCE TO RELATED APPLICATION

This application claims the benefit of and priority to French Patent Application No. 1355126, filed Jun. 4, 2013. French Patent Application No. 1355126 is hereby incorporated by reference in its entirety.

BACKGROUND

The present disclosure relates to "active implantable medical devices" as defined by Directive 90/385/EEC of 20 Jun. 1990 of the Council of the European Communities, including implantable devices for continuous monitoring of the heart rhythm and delivery of electrical stimulation or resynchronization pulses to the heart if necessary. It relates more specifically to pacemaker leads to be implanted in the cardiac coronary network to allow stimulation of a left, ventricular or atrial cavity.

Unlike in right cavities, when it is desired to stimulate a left cavity, it is usually chosen to introduce a lead not into the cavity to be stimulated but in the coronary network. The lead is provided with an electrode applied against the wall of the epicardium and oriented towards the left ventricle or the left atrium, as appropriate.

Such a lead is for example the Situs LV model, marketed by Sorin CRM (Clamart, France) and described in EP0993840 A1 (Sorin CRM, previously known as ELA Medical). The introduction of such a lead is made by the coronary sinus opening in the right atrium, by endocardial access. The lead is then oriented and pushed along the coronary venous network to the selected pacing site. This intervention is very difficult given the particularities of the venous network and its access paths. These particularities may include the passage of valves, the tortuosity, and the gradual reduction in diameter of the conduit as the lead progresses into the selected coronary vein.

Once the target vein is reached, a satisfactory stimulation site must be found and it must be ensured that the chosen stimulation point does not generate phrenic stimulation.

In addition, a trend in recent developments in left ventricle pacing leads is the reduction of the diameter of the implantable part in the coronary network. The size of the lead body is indeed a factor directly related to the controlled guiding capacity of the lead in the venous coronary network, to be able to select specific stimulation sites located in certain collateral veins.

Thus, EP 2581107 A1 (Sorin CRM SAS) describes a lead including in its active distal part a microcable having a diameter of the order of 0.5 to 2 French (0.17 to 0.66 mm). This microcable includes an electrically conductive core cable formed by one or more strands of a plurality of composite strands, with a polymer insulation layer partially surrounding the core cable. The isolation layer is punctually exposed so as to expose the microcable in one or more points constituting a network of electrodes connected in series. The free end of the strand is also provided with a reported distal electrode.

EP 2455131 A1 (Sorin CRM SAS) discloses a lead of the same type, wherein the microcable slides in a lumen of a lead body, from which it can emerge over a length of 1 to 200 mm beyond the outlet of the lead body. The distal end of the lead body is provided with a sleeve of silicone assisting with its retention in a median region of the target vessel. From this position, the microcable is deployed into the vessel up to its distal active part (including the exposed portions forming the electrodes network) until it reaches the target region in a deep area of the coronary network.

In another embodiment described therein, the lead includes a plurality of microcables housed in as many separate respective lumens of a same lead body. The openings of the different lumens are axially shifted on the lead body, thus having a plurality of lateral openings from which the active parts of each of the microcables successively emerge.

One advantage of the very small diameter of the microcable is that it allows exploiting the entire length of the vein and cannulation of veins of very small diameter. Such areas have generally not been exploited until now due to the excessive size of conventional coronary leads. It, thus, becomes possible to treat areas difficult to reach, thereby making optimal use of all the veins present in the basal area. This may also lessen the risk of phrenic nerve stimulation which generally increases when the lead is too distal.

Moreover, the multiplication of stimulation points in a deep zone of the coronary network allows (unlike traditional leads) simultaneous stimulation of multiple zones of the epicardium in the region of stimulation, thereby improving the chances of optimal myocardium resynchronization.

With such a microlead, it is even possible to cross anastomosis (passages present from the end of certain veins to another vein), with the possibility of advancing the microlead in a first vein ("go" vein) followed by an anastomosis into a second vein ("return" vein) going back thereof. This may allow stimulation of the left ventricle from two distinct and remote regions. Finally, the structure of this microlead gives it great strength that guarantees its long-term biostability.

One of the difficulties with this type of microlead lies in the evaluation of the electrical stimulation site before the final placement of the microlead. Indeed, the implantation of a microlead of the aforementioned type is based on the use of a very thin catheter introduced to the target vein by conventional technique, with introduction of a guidewire into the venous system. The implantation proceeds by threading the catheter over this guidewire and finally by removal of the guidewire. The catheter in place helps guide the microlead to the stimulation site, and then this catheter is removed to expose the electrodes of the microlead and thus make them functional. This procedure does not allow anticipating the stimulation performance quality before the electrodes of the microlead are exposed in the final position thereof. Furthermore, this type of lead including a microcable does not have a very good tracking performance, that is to say the ability to progress into the venous system by push and torsion manipulation of its proximal end.

A microcable is indeed much more deformable than a guidewire, which is specially designed to navigate into the venous system. A guidewire typically has the required properties of "torquability" (ability to transmit over its entire length to the distal end a rotation given by an operating handle from the proximal end) and "pushability" (ability to progress in the biological network without jamming, under the effect of a push exerted from the proximal end with the operating handle). These properties are important for navigation in the coronary network.

It is therefore very difficult to introduce and guide a microcable directly into the venous system. For these reasons, it is also very difficult to change the position once it has been set up, such as in searching for better stimulation sites. Further, it is extremely difficult to make it go back to then select another vein or pass through an anastomosis.

It is thus desirable to evaluate as early as possible during the implantation procedure the best placement position of the microlead and its electrodes, to be able, if necessary, to modify this position or even to consider repositioning the microlead in another vein of the coronary network.

SUMMARY

An exemplary embodiment combines a microcable with an implantable catheter that remains in position after implantation. Such a catheter is therefore different from the conventional catheters, which are not intended to remain in place beyond the implantation of the lead. This implantable catheter, hereinafter designated "microcatheter," acts as an insulator for the microcable and is provided with one or more windows formed in the wall of the microcatheter. These windows locally allow the transmission of a stimulation electrical field and thereby define the stimulation zones of the microlead. The "microlead" as used herein being understood as the combination of the microcable and the microcatheter.

The microcable and the microcatheter are separable because they are intended to be implanted sequentially, not simultaneously as in the case of a microcable microlead provided with an insulation layer. Moreover, the introduction of the microcable in the microcatheter leaves a possibility of relative axial movement (telescopic function) so as to move the windows, and thus the stimulation zones, once the assembly is set up into the vein.

Furthermore, according to one aspect of the invention, the electrical evaluation of the stimulation areas can be performed immediately after the implantation of the microcatheter, and before the introduction of the microcable. The guidewire used to place the microcatheter is left in place during the time of this evaluation. In this configuration, the guidewire (of metal material) will act as an electrical conductor positioned adjacent to the microcatheter windows. The physician can then reposition the stimulation areas by moving forwards or backwards the microcatheter along the guidewire.

If the selected channel does not offer a satisfactory stimulation threshold, the physician can then back or retract the microcatheter to discover the end of the guidewire. Another anastomosis can then be selected with this guidewire, and the physician can then quickly repeat the evaluation of a new vein without the need to remove the guidewire or the microcatheter. It thus becomes possible to optimize the time of implantation by a rapid assessment of the site of stimulation. This also provides more opportunities to the doctor in the eventual choice of anastomosis and in the position of the stimulation areas, even before the introduction of the microcatheter.

Once the doctor has confirmed the stimulation position, he need only replace the guidewire by the microcable to complete the implant procedure. The windows of the microcatheter are in an unchanged position during this substitution, and the position of the site has not been changed and remains the one used for the electrical evaluation.

More specifically, exemplary embodiments of the invention disclose a system, implantable into the coronary venous network, for the stimulation of a left heart chamber using a generator of an active implantable medical device, especially a cardiac pacemaker or resynchronizer. This system includes a microcable of a conductive material, including in the proximal portion a connector for coupling the microcable to the generator of the active implantable medical device. The system also includes a catheter of an insulating material, including a hollow tube housing the micocable in an internal lumen with possibility of relative axial translation between the catheter and the microcable.

In preferred embodiments, the catheter is an implantable microcatheter of a diameter at most equal to 2 French (0.66 mm), made of biocompatible material (s) suitable for permanent implantation in venous networks. At its distal portion, it includes at least one lateral window including a through hole formed on the wall of the hollow tube, and adapted to be adjacent to, or face, without a galvanic barrier, a region of the surface of the microcable located in said inner lumen at the limit of this window with a stimulation site defined on the wall of the target venous facing the microcatheter window, said region of the microcable forming a stimulating electrode. In its distal part, the microcable is a non-insulated microcable, at least in the region of the window of the microcatheter. Furthermore, the microcatheter can be telescopically moved on the microcable in said distal portion between an extended position, having in proximity the respective distal ends of the microcable and of the microcatheter, and a retracted position, having a distance between said respective distal ends, so as to modify the position of said stimulation site of the target vein by the effect of the movement of the microcable on the microcatheter.

The through hole of the side window(s) can be a vacuum orifice, defining a free space, or can be filled with an electrically conductive material. In either case, this orifice locally authorizes the transmission of the stimulation electrical field and thus defines a stimulation area of the microlead.

According to various advantageous subsidiary features or characteristics:

In the extended position, the microcable does not emerge beyond the distal end of the hollow tube of the microcatheter;

The microcatheter includes in its proximal region a connecting system to secure the microcable in a final, relative axial position between the extended position and the retracted position;

The microcable includes at least one conformation sleeve, sheathing the microcable in a region thereof remote from the window of the microcatheter;

The movement path of the microcatheter on this microcable between the extended position and the retracted position is at most 50 mm;

The unitary surface of the at least one side window is at least 0.2 $mm^2$, and if the system includes a plurality of side windows, their combined surface is at most 6 $mm^2$; and The microcatheter includes at least one group of a plurality of side windows circumferentially distributed in a same axial position of the hollow tube.

According to another aspect of the invention, the system further includes a non-implantable removable guidewire. This guidewire is adapted, after having been previously introduced into the coronary venous system to a target vein, to receive the hollow tube of the microcatheter threaded over, and allows by sliding the guiding of the microcatheter until the target vein. The guidewire is of a non-insulated conductor material, and is provided at its proximal portion with a coupling mechanism to couple the guidewire to a stimulation pulse generator. The microcatheter is adapted to be telescopically moved over the guidewire between extended and retracted positions, so as to define said stimulation site on the wall of the target vein facing the microcatheter window. The guidewire in the region of the window forms a stimulation electrode.

According to another aspect of the invention, a method for implanting a microlead to provide stimulation to a chamber of the heart by a generator of an active implantable medical device includes introducing an insulated catheter comprising a hollow tube having an internal lumen into the coronary venous system of a patient, the catheter further comprising at least one lateral window comprising a through orifice formed on the wall of the hollow tube. The method further includes introducing a microcable of a conductive material, comprising in a proximal portion a connector for coupling to the generator of the active implantable medical device into the internal lumen of the catheter, wherein the microcable and the catheter are configured to allow relative axial translation between the microcable and the catheter. The method also includes positioning the catheter such that the lateral window is aligned with a stimulation site on the wall of the target vein, and a region of the microcable surface located in the internal lumen at the lateral window forms a stimulation electrode.

According to another aspect of the invention, a system implantable into a chamber of the heart includes a microcable made of a conductive material and a catheter made of an insulating material, the catheter comprising a hollow tube forming an internal lumen. The catheter is further configured to be positioned over a guidewire and, with the guidewire removed, receive the microcable in the internal lumen. The catheter is an implantable microcatheter configured to remain in the venous network, and the microcatheter comprises at least one aperture formed in the wall of the hollow tube. A region of the microcable adjacent to the aperture forms a stimulation electrode. The microcatheter is adapted to be moved on the microcable so as to modify the position of the aperture, and thereby modify the position of the stimulation electrode, relative to the microcable.

DETAILED DESCRIPTION

Figure 1:
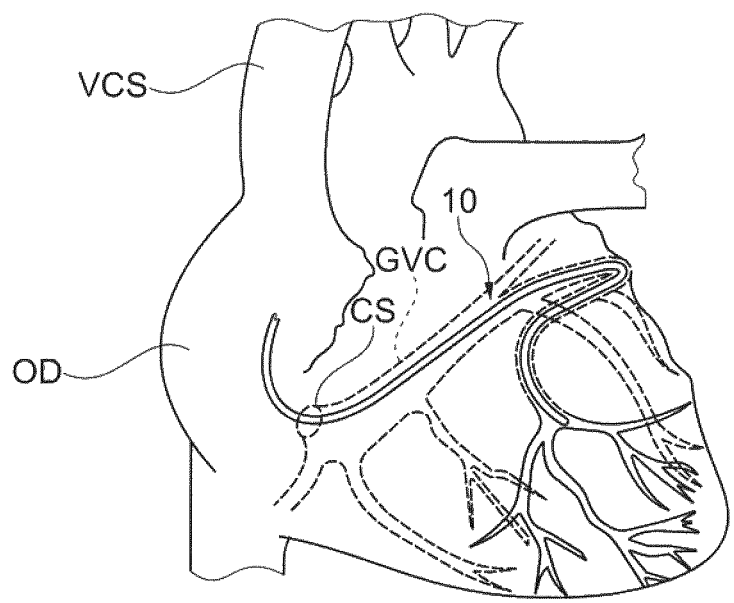
FIG. 1 generally illustrates the myocardium, with the main veins of the coronary network, wherein a microlead has been introduced according to the invention for the stimulation of a left cavity of the heart.

FIG. 1 generally illustrates the myocardium and the major vessels of the coronary network in which a microlead 10 was introduced. Microlead 10 was introduced by endocardial access via the superior vena cava VCS, the right atrium OD, the input of venous coronary sinus CS and the great cardiac vein GVC. The microlead 10, which is described in detail below, has a diameter at most equal to 2 French (0.66 mm), typically about 0.5 to 2 French (0.16-0.66 mm). Microlead 10 has in its distal part a plurality of detection/stimulation electrodes intended in particular to stimulate the left ventricle from the one or more corresponding sites located in a vein of the deep coronary network. If needed, stimulation by microlead 10 may occur after passing through an anastomosis (an anastomosis is an existing passage, at the end of certain veins of the coronary system, to another vein, with the possibility of communication between two separate veins at the anastomosis, via their respective distal ends). With such a configuration, it is possible not only to stimulate the left ventricle from points located deep in a vein of the coronary network, but also through the anastomosis in proximal regions of veins in which it would have been difficult to stabilize or anchor conventional left ventricle pacing leads.

Figure 2:
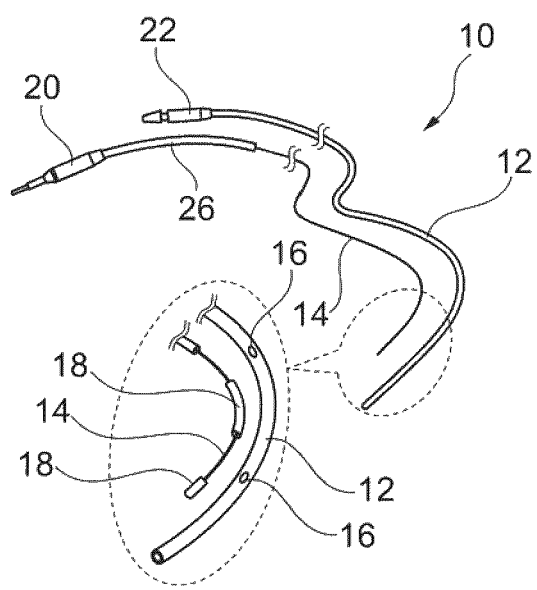
FIG. 2 is an overview of the microlead of the invention with its two separate elements, the microcatheter and the microcable, including an enlarged view of the distal portion of the two elements thereof.

FIG. 2 generally illustrates the structure of the microlead 10 of the invention, which includes a microcatheter 12 having a hollow tube in which a microcable 14 is introduced in the lumen under conditions described below. In its distal portion (shown more clearly visible in the detail of FIG. 2), the microcatheter 12 is provided with one or more windows 16 formed by a through hole formed on the wall of the hollow tube.

This window, or each of these windows (in the example below it is assumed that there are several), allows a region of the surface of microcable 14 housed in the hollow tube of the microcatheter 12 in line with this window 16 to be compared or aligned, without galvanic barrier, with a stimulation site. The stimulation site is defined on the wall of the target vein next to the window 16, and the region of the microcable 14 thereby forms a sensing/pacing electrode.

The orifice of the window 16 may be empty, that is to say be left unchanged by defining a free volume after removal of the microcatheter material at the location of the windows 16. Alternatively, the window 16 may be filled with an electrically conductive material such as a conductive polymer or a metal element included in the section of the microcatheter 12. But in either case, this orifice is such that it locally authorizes the transmission of the stimulation electric field and in this method defines a stimulation area of the microlead.

Microcable 14 may include a full, electrically conductive, core cable having a composite structure formed from a plurality of strands or a plurality of elementary strands combining a structuring material and a radiopaque material. The microcable 14 preferably has between 15 and 300 elementary strands. The structuring material may be a stainless steel including a cobalt alloy, a noble metal, a titanium, or a NiTi alloy having a high fatigue resistance. Such materials may provide the properties of strength, flexibility, fatigue resistance, etc., and a good electrical conductivity to the microcable 14. The radio-opaque material, for making the microcable X-ray visible during its introduction by the physician, may be selected from the group including or consisting of: tantalum, tungsten, iridium, platinum, gold and their alloys.

Furthermore, methods of gradual rigidity reduction are provided along the microcable between its proximal portion and its distal portion, e.g. by a stepped stacking of tubes nested one inside the other, or by a series of isodiameter tubes of increasing rigidity. The resulting rigidity gradient ensures, firstly, a non-traumatic flexible distal portion to monitor all the tortuosity of the deep coronary network. Secondly, it provides a more rigid proximal portion for transmitting the thrust exerted by the doctor by suitable devices.

In the free state, the microcatheter may be rectilinear or, preferably, shaped, for example by specific sleeves 18 sheathing the microcable in a region thereof that is not electrically active (not situated in line with a window 16 of the microcatheter 12).

Finally, at its proximal end the microcable 14 is provided with a connector 20, for example of the IS-1 type, including an electrical terminal connection to the generator a cardiac implant such as a pacemaker or a resynchronizer.

Unlike the microcable disclosed in EP 2581107 A1 cited above, the microcable 14 of the invention has no insulation layer, at least in its distal portion located opposite the windows 16 of the microcatheter 12. Indeed, as discussed more specifically in the detailed description below, the microcatheter 12 acts as an insulator, interposed (except locally at the location of the windows 16) between the microcable 14 and the surrounding cardiac tissues. It is therefore not necessary that the microcable is isolated, at least in its active distal part. The insulation, e.g. a PET layer, may only be present in the proximal, not active, portion up to the connector 20, as shown at 26 in FIG. 2.

The microcatheter 12 is an implantable microcatheter, that is to say, it is suitable for and intended to be left in place after implantation of the microlead. Preferably, it has conferred properties of implantability that conventional catheters used for these procedures do not have (catheters that serve only during the implantation). By "implantability," it must be understood to have the ability to be permanently implanted in the coronary system, safely for the patient, both in the chosen material (which must be biocompatible and blood compatible in particular) and with the absence of mechanical hazards. It should maintain these abilities for a period of up to several years. The microcatheter should be able to withstand without breaking typically 400 million instances of bending stresses, a value corresponding to the average number of heart beats on the design life of the microlead (10 years). In other words, the microcatheter should be able to pass the permanent implantability tests so far reserved for leads, including: biocompatibility compliant to ISO 10993 (medical devices in general) and compliance to EN 45502 (concerning especially the leads) for corrosion, lack of risk of rupture and, in case of rupture, safety for the patient.

Such an implantable microcatheter 12 can include, for example, a polymer tube provided at its proximal end with a tightening or connecting system 22, for example by ligature. The tightening system is configured to allow at the end of surgery axially fastening the microcable 14 to the microcatheter 12 which has been introduced inside the lumen of the microcatheter 12, thus preventing any substantial relative axial movement of these two elements.

The tube of the microcatheter 12 has a gradually reduced section, from e.g. approximately $Ø_1$=1.3 mm in the proximal portion to approximately $Ø_2$=0.5 to 1.0 mm in the distal portion. The structure of the microcatheter 12 preferably presents no discontinuity in the longitudinal direction, such as any welding or bonding, to minimize the risk of fatigue failure. In this way, the microcatheter 12 may attain great flexibility in the distal portion and greater stiffness in the proximal portion, and the transition from one part to the other being obtained continuously without creating risk of local excessive stress in handling.

The microcatheter tube 12 is preferably made by an extrusion technique at variable speed of two materials. The inside of microcatheter tube 12 defines an inner lumen, which may be made of, for example PTFE—a material selected for its properties of: very low friction coefficient (thus facilitating the insertion and removal of the microcatheter 14 into the internal lumen), its ability to be extruded in polyurethane with a very small thickness, and its mechanical flexibility. On the outside, the PTFE tube receives an extrusion coating, for example of polyurethane—a material selected for its properties of flexibility, mechanical strength, abrasion resistance, ability to be extruded and biocompatibility. It is possible to provide on the outer surface of a microcatheter a biocompatible coating improving the sliding against the vessel walls, for example a hydrophilic coating of the polyvinylpyrrolidone-type (PVP) or a silicone. The surface coating may also be selected to enhance biocompatibility with the living environment, by addition of antimicrobial and hemocompatible agents preventing thrombosis formation, for example a coating of a thin carbon film.

Figure 3:
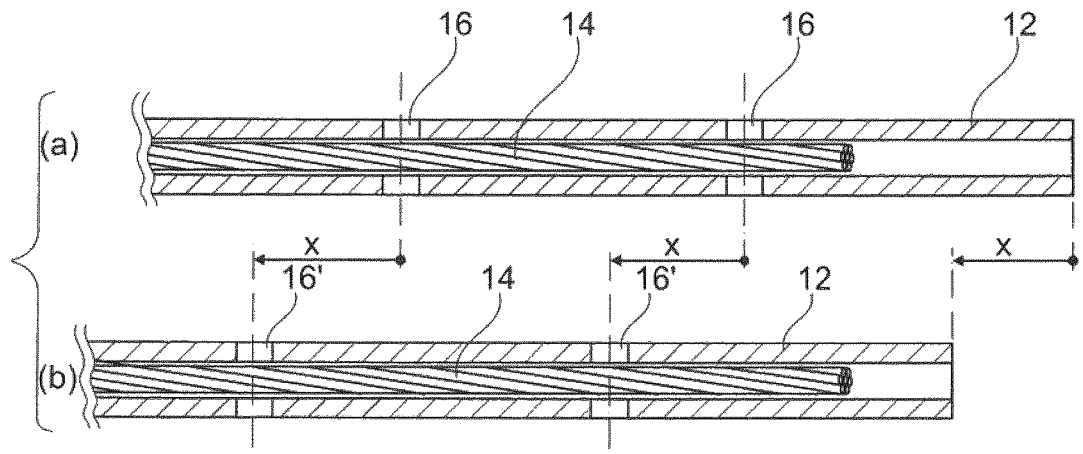
FIG. 3 illustrates the possibility of movement of the microcatheter on the microcable, for the local adjustment of the stimulation zones.
Figure 4:
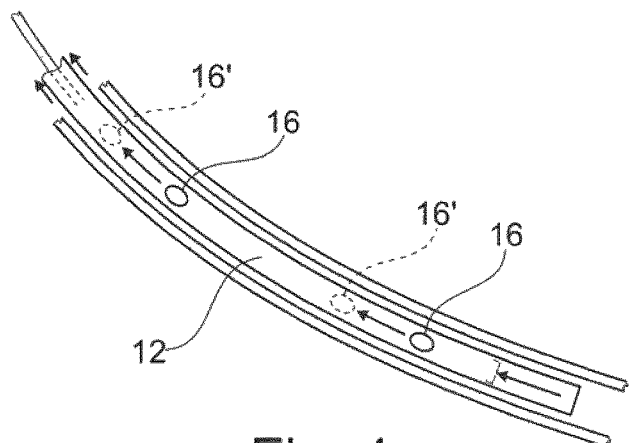
FIG. 4 also illustrates the possibility of adjustment shown in FIG. 3, with the microcatheter in place in the coronary vein.

FIGS. 3 and 4 illustrate the possibility of movement of the microcatheter on the microcable, for local adjustment of the stimulation areas. It is seen that the relative configuration of the microcable 14 and of the microcatheter 12 (which together form the stimulation microlead of the invention) may be modified by axially moving the microcatheter 12 relative to the microcable 14. It is intended that the microcable 14 remains fixed. The displacement of x amplitude is typically between 0 and 50 mm and allows modifying, in 16', the position of the windows 16, and thus the stimulation sites, with respect to the vessel wall where the microlead is implanted. This telescopic movement feature particularly permits adjustment of the position of the stimulation windows according to the electrical performances found during implantation, so as to optimize the pacing thresholds, the position of the electrodes, to avoid phrenic nerve stimulation, etc.

Figure 5:
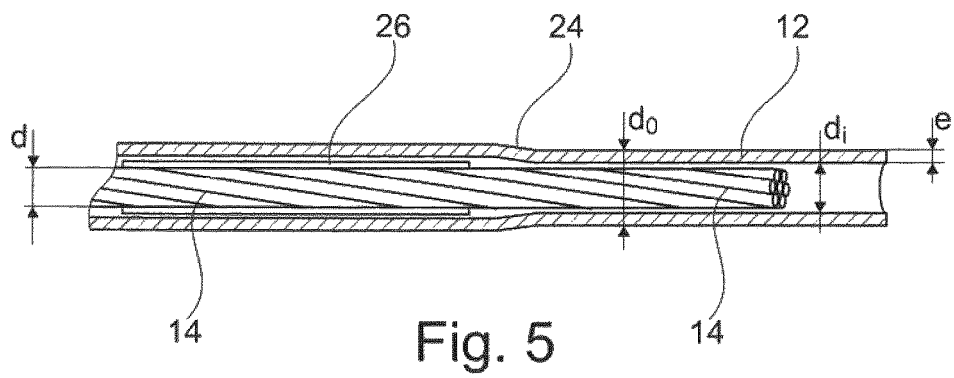
FIG. 5 illustrates the various diameters of the microcatheter/microcable system in the distal region of the lead of the invention.

FIG. 5 shows a sectional view with the various diameters of the microcatheter 12/microcable 14 combination, with dimensions, purely illustrative, that can be, for example, the following:

Diameter d of microcable: 0.3 mm for the exposed microcable, and 0.34 mm in a non-active region wherein it is coated with an insulating layer 26;
Inner diameter $d_i$ of the microcatheter 12: 0.35 mm;
Outer diameter $d_o$ the microcatheter 12: 0.50 mm; and
Microcatheter thickness: 0.125 mm, reduced to 0.075 mm in the distal portion to maintain a substantially constant diameter.

A cone 24 optimizes the transition between the area coated with an insulating layer 26 and the area wherein the microcable 14 is exposed, so as to approach closer to the conductor. It is indeed important to place the conductive surface of the microcable 14 closer to the vein wall in the region of the window of the microcatheter 12. This may be achieved especially by reducing the clearance between the microcable 14 and the microcatheter 12 (maximum clearance of 0.1 mm on the diameter) and reducing the thickness of the microcatheter in the most distal portion.

Figure 6A:
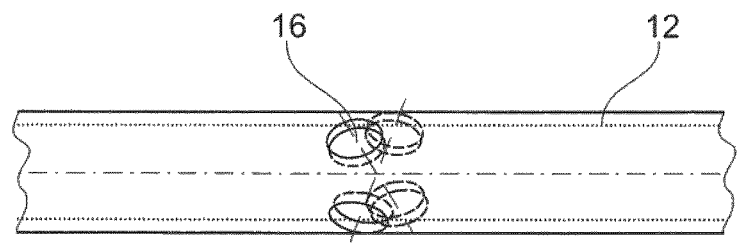
FIGS. 6a to 6f illustrate various possible embodiments of the windows formed in the microcatheter of the lead of the invention.
Figure 6B:
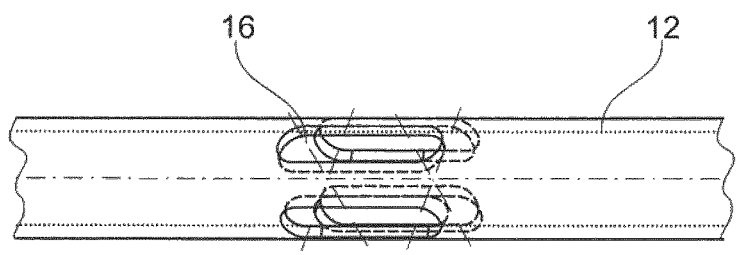
Figure 6C:
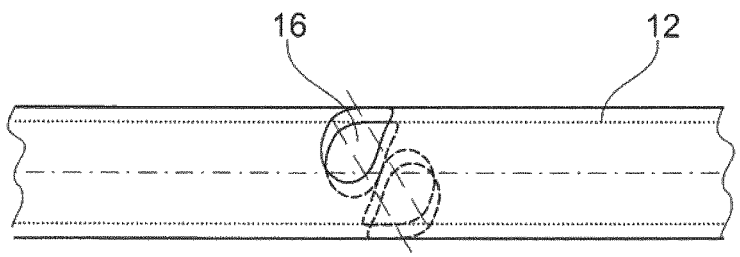
Figure 6D:
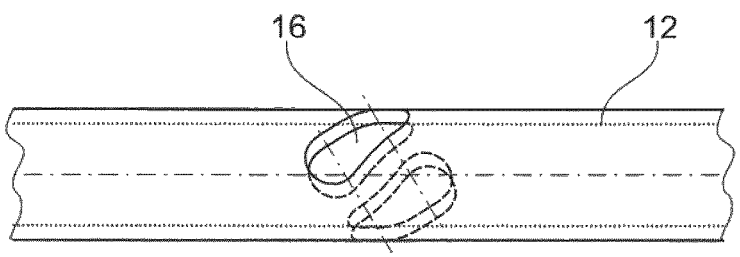
Figure 6E:
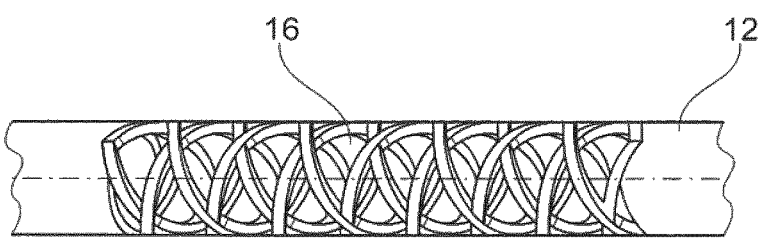

FIGS. 6a to 6f show various possible embodiments of the windows 16 formed in the microcatheter 12 of the lead 10 of the invention. These windows 16 can notably be formed by:

Four circular holes, circumferentially distributed at 90° (FIG. 6a);
Four slots distributed circumferentially at 90° (FIG. 6b);
Two slots distributed circumferentially at 90° (FIG. 6c);

Two slots distributed circumferentially at 180° and having an inclination of 45° relative to a circumferential direction (FIG. 6d);

Multiple openings formed on a length of 10 mm, for example (FIG. 6e) or

Figure 6F:
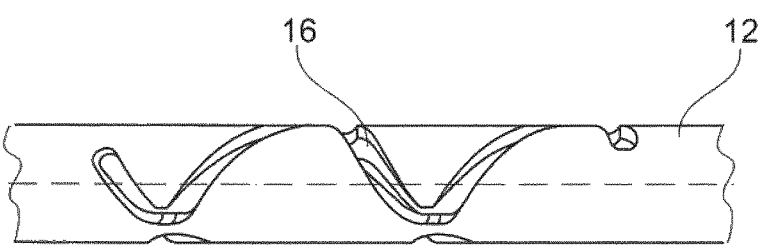

Two semi-helical openings at 180° (FIG. 6f).

Each of the windows 16 may be made for example by laser ablation on the extruded tube. The minimum surface for satisfactory stimulation is on the order of 0.2 mm² per window, preferably with a maximum aggregate surface of not more than 6 mm² for the whole of the microlead.

Finally it must be noted that it is possible to consider many variants of the microcatheter/microcable configuration according to the invention as described above. In particular, if the configuration described is a monopolar microlead with a single conductor simultaneously delivering pulses to the various stimulation sites, it is also possible to envisage a multipolar configuration. In the latter case, the microcatheter includes several separate conductors, insulated from each other and selectively activatable by the corresponding terminals of the generator. The different conductors of the microcable then arise adjacent to the respective windows of the microcatheter. These windows corresponding to stimulation sites, or groups of stimulation sites, each independently activatable.

Figure 7:
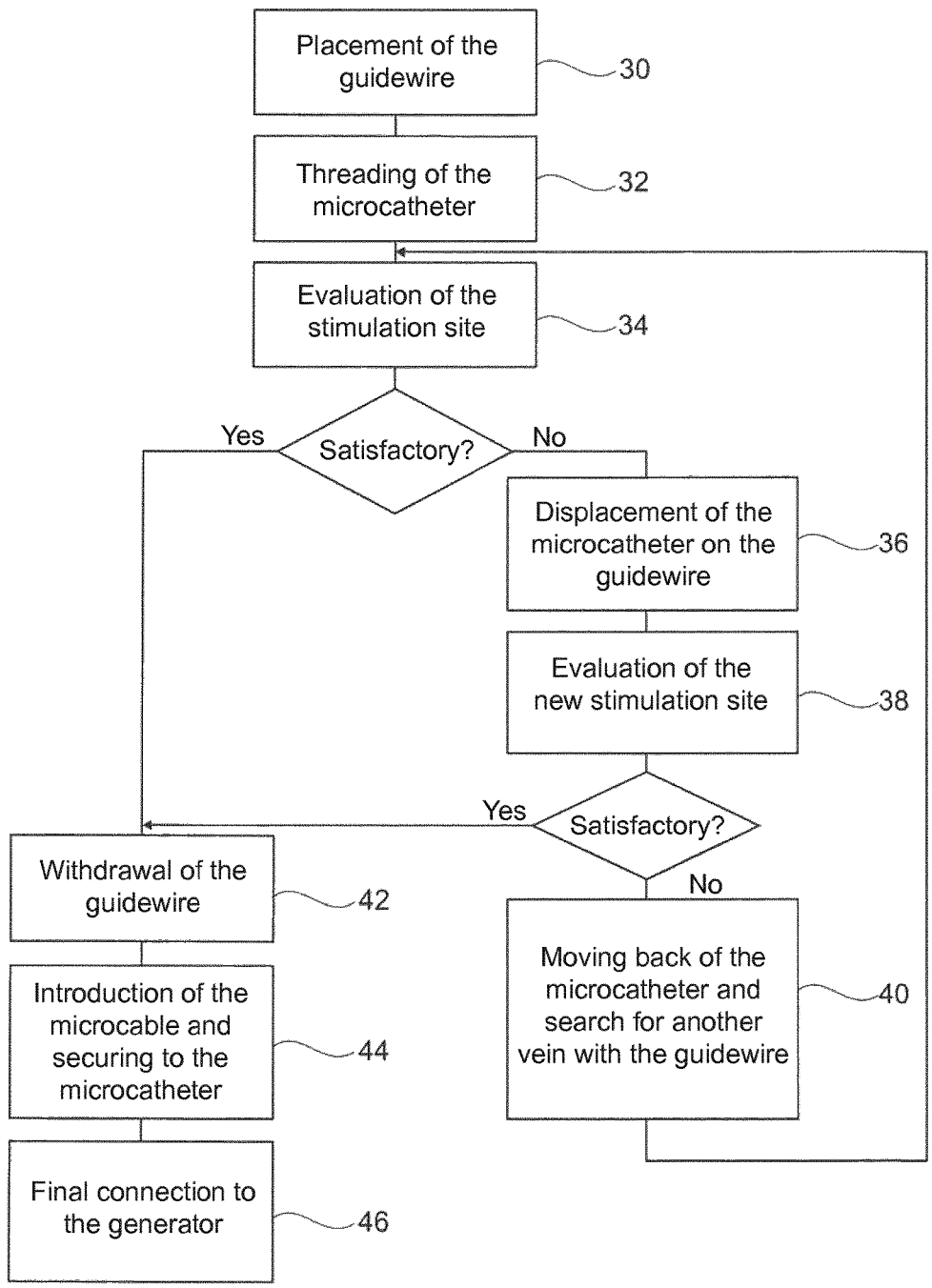
FIG. 7 is a flow chart explaining the successive steps of the implantation procedure of the microlead according to the invention.

FIG. 7 is a flow chart explaining the successive steps of the implantation procedure according to the microlead of the invention. Implantation begins by the placement of the microcatheter 12, by a conventional OTW (over the wire) technique, by using a very fine stylet forming a guide-wire. The guide-wire may be provided with an atraumatic termination at its distal end for its direct introduction into the vessels of the coronary system without risk of perforation.

First, the doctor has a main catheter allowing access at the mouth of the coronary sinus CS. A sub-selection catheter is then used to select, with help of an image intensifier, the path in the coronary venous network that will allow reaching the target vein. The doctor then inserts the guidewire through the sub-selection catheter, and pushes this guidewire to advance, in the coronary venous system in order to select a particular collateral vein (step 30). The guidewire may possibly be advanced to an anastomosis with the crossing of this anastomosis and progression in the selected "go back" vein.

The physician then positions on the guidewire the microcatheter 12 according to the invention, and slides it forward on this guidewire until the end thereof (step 32), taking care that at the distal side the entire length of the guidewire is covered with the microcatheter 12. In a conventional procedure, the physician then withdraws the guidewire, leaving in place the microcatheter 12 to allow introduction of a microlead. This is not the procedure chosen in the case of the invention.

Indeed, insofar as the guide wire is completely covered by the microcatheter, it has electrically the same behavior as the microcable that will later be pushed through the microcatheter. That is to say, in the regions of the windows 16 of the microcatheter 12, the guidewire will be adjacent to the opposite wall of the target vein without obstacle, therefore with possibility of having an area of stimulation at this location if the guidewire is connected to a pulse generator. For this, the guidewire, which is a wire of an non insulated conductive material, is provided at its proximal portion with a coupling mechanism to couple the guidewire to a stimulating pulse generator.

The doctor can thus evaluate the effectiveness of the stimulation site (step 34) directly with the guidewire and through the windows of the microcatheter 12. If the site is not satisfactory, the microcatheter 12 is moved back over the guidewire to move the position of the windows, in the same method as what has been described and illustrated in FIGS. 3 and 4 above (but in this case, with the guidewire inserted into the lumen of the microcatheter 12 instead of the microcable 14). The new site of stimulation, with the moved back microcatheter 12, is subject to further evaluation (step 38).

If no position of the microcatheter in its telescopic movement relative to the guidewire provides a satisfactory stimulation, the doctor more widely moves back the microcatheter 12 to on the guidewire. He may then select another vein (step 40). The microcatheter 12 is then repositioned so as to completely cover the guidewire, then the evaluation procedure described above is repeated, with the position adjustment of the stimulation site by telescopic movement of the microcatheter 12 into the guidewire in the newly selected vein (steps 34, 36, 38).

When a satisfactory stimulation site is found, the guidewire is completely removed (step 42), only leaving in place the microcatheter 12 in an unchanged position. In this position, the windows 16 define the position of the satisfactory stimulation site. The microcable 14 is then introduced into the microcatheter 12, replacing the guidewire, and secured in the axial position to the microcatheter 12 by a connecting or tightening system 22, for example by ligature (step 44).

The microlead 10 according to the invention with the microcable 14 and the microcatheter 12, whose windows 16 were carefully moved to the most powerful stimulation site, is then connected to the cardiac pacemaker or resynchronizer generator (step 46).

The invention claimed is:

1. A system implantable into the coronary venous network for the stimulation of a left chamber of the heart by way of a generator of an active implantable medical device, the system comprising:

a microcable of a conductive material, comprising in a proximal portion a connector for coupling the microcable to the generator of the active implantable medical device; and a catheter of an insulating material, comprising a hollow tube housing in an internal lumen the microcable with possibility of relative axial translation between the microcable and the catheter;

wherein the catheter is an implantable microcatheter of a diameter at most equal to 2 French (0.66 mm), made of biocompatible material(s) suitable for permanent implantation in the venous network;

wherein the microcatheter comprises, in a distal portion, a plurality of lateral windows comprising a through orifice formed on a wall of the hollow tube, and adapted to be adjacent to, without galvanic barrier, a region of the microcable surface located in said internal lumen at the plurality of lateral windows;

wherein the plurality of lateral windows align with a stimulation site on the wall of the target vein facing the microcatheter, and the region of the microcable forms a stimulation electrode;

wherein the microcable, in a distal portion, is a continuous non-insulated microcable across an entire length of the microcable spanning between a proximal-most window and a distal-most window of the catheter; and wherein the microcatheter is adapted to be telescopically moved on the microcable in said distal portion between an extended position, wherein the respective distal ends of the microcable and of the microcatheter are in proximity, and a retracted position, wherein the distal end of the microcatheter is remote from the distal end of the microcable, so as to modify the position of said stimulation site of the target vein by the effect of the movement of the microcatheter on the microcable.

2. The system of claim 1, wherein the through orifice of at least one side of the plurality of lateral windows of the microcatheter is an empty orifice defining a free volume.

3. The system of claim 1, wherein the through orifice of at least one lateral window of the microcatheter is a hole filled with an electrically conductive material.

4. The system of claim 1, wherein in the extended position, the microcable does not emerge beyond the distal end of the hollow tube of the microcatheter.

5. The system of claim 1, wherein the microcatheter further comprises in its proximal region a connecting system to secure the microcable in a relative, final, axial position between the extended position and the retracted position.

6. The system of claim 1, wherein the at least one microcable comprises a shaping sleeve, sheathing the microcable in a region thereof remote from the plurality of windows of the microcatheter.

7. The system of claim 1, wherein the displacement path of the microcatheter in the microcable between the extended position and the retracted position is at most 50 mm.

8. The system of claim 1, wherein a unit surface of one of the plurality of lateral windows is at least 0.2 mm$^2$.

9. The system of claim 1, wherein an aggregate surface of the plurality of lateral windows is not more than 6 mm$^2$.

10. The system of claim 1, wherein the microcatheter has at least one group of the plurality of lateral windows circumferentially distributed in a same axial position of the hollow tube.

11. The system of claim 1, further comprising:
a non-implantable removable guidewire, this guidewire being adapted, after having been previously introduced into the coronary venous system to a target vein, to receive the hollow tube of the microcatheter threaded over, and allow by translation guiding of the microcatheter to the target vein; wherein:
the guidewire is of a non-insulated conductor material, and is provided at its proximal portion with a coupling mechanism for coupling to a stimulation pulse generator;
the microcatheter is adapted to be telescopically moved on the guidewire between said extended and retracted positions, so as to define said stimulation site on the wall of the target vein adjacent to the window of the microcatheter, the guidewire in the region of the window forming a stimulation electrode.

12. The system of claim 1, wherein the hollow tube of the catheter has a gradually reduced diameter between the proximal portion and the distal portion.

13. The system of claim 1, wherein the rigidity of the microcable is gradually reduced from the proximal portion to the distal portion thereof.

14. A method for implanting a microlead to provide stimulation to a chamber of the heart by a generator of an active implantable medical device, comprising:
introducing an insulated catheter comprising a hollow tube having an internal lumen into the coronary venous system of a patient, the catheter further comprising a plurality of windows comprising a through orifice formed on a wall of the hollow tube;
introducing a microcable into the internal lumen of the catheter, wherein the microcable is of a conductive material, comprises in a proximal portion a connector for coupling to the generator of the active implantable medical device, and in a distal portion is a continuous non-insulated microcable across an entire length of the microcable spanning between a proximal-most window and a distal-most window of the catheter, wherein the microcable and the catheter are configured to allow relative axial translation between the microcable and the catheter; and
positioning the catheter such that the lateral window is aligned with a stimulation site on a wall of the target vein, and the distal portion of the microcable surface located in the internal lumen at the lateral window forms a stimulation electrode.

15. The method of claim 14, wherein positioning the catheter comprises moving the catheter between an extended position, wherein the respective distal ends of the microcable and of the catheter are in proximity, and a retracted position, wherein the distal end of the catheter is remote from the distal end of the microcable, so as to modify the position of said stimulation site.

16. The method of claim 15, wherein in the extended position, the microcable does not emerge beyond the distal end of the hollow tube of the microcatheter.

17. The method of claim 14, further comprising:
prior to introducing the catheter, introducing a guidewire into the coronary venous system;
introducing the catheter into the coronary venous system over the guidewire such that a distal end of the guidewire is covered by the catheter;
coupling the guidewire to the generator of the active implantable medical device;
positioning the catheter such that the plurality of lateral windows are aligned with a stimulation site on the wall of the target vein, and a region of the guidewire surface located in the internal lumen at the lateral window forms a stimulation electrode; and
removing the guidewire while maintaining the position of the catheter.

18. The method of claim 17, wherein evaluating the effectiveness of the stimulation site comprises moving the catheter relative to the guidewire so as to modify the position of the stimulation site.

19. The method of claim 14, further comprising using a connecting system to axially secure the microcable to the catheter.

20. A system implantable into a chamber of the heart, comprising:
a microcable made of a conductive material; and
a catheter made of an insulating material, the catheter comprising a hollow tube forming an internal lumen, the catheter configured to be positioned over a guidewire and, with the guidewire removed, the catheter receives the microcable in the internal lumen;
wherein the catheter is an implantable microcatheter configured to remain in the venous network;
wherein the microcatheter comprises a plurality of lateral windows formed in the wall of the hollow tube;
wherein a region of the microcable positioned in the microcatheter and adjacent to the plurality of windows forms a stimulation electrode via a continuous non-insulated distal portion of the microcable across an entire length of the microcable spanning between a proximal-most window and a distal-most window of the catheter; and
wherein the microcatheter is adapted to be moved on the microcable so as to modify the position of the plurality of lateral windows, and thereby modify the position of the stimulation electrode, relative to the microcable.

* * * * *